United States Patent
Liang et al.

(10) Patent No.: US 12,083,206 B2
(45) Date of Patent: Sep. 10, 2024

(54) HAIR TREATMENT COMPOSITIONS

(71) Applicant: L'OREAL, Paris (FR)

(72) Inventors: Jun Liang, Staten Island, NY (US); Heather Yoonsoo Lee, Wayne, NJ (US)

(73) Assignee: L'OREAL, Paris (FR)

( * ) Notice: Subject to any disclaimer, the term of this patent is extended or adjusted under 35 U.S.C. 154(b) by 178 days.

(21) Appl. No.: 17/331,904

(22) Filed: May 27, 2021

(65) Prior Publication Data
US 2021/0369579 A1    Dec. 2, 2021

Related U.S. Application Data

(60) Provisional application No. 63/032,025, filed on May 29, 2020.

(30) Foreign Application Priority Data

Jul. 16, 2020 (FR) .................... 2007471

(51) Int. Cl.
| | |
|---|---|
| A61K 8/34 | (2006.01) |
| A61K 8/04 | (2006.01) |
| A61K 8/36 | (2006.01) |
| A61K 8/41 | (2006.01) |
| A61Q 5/00 | (2006.01) |
| A61Q 5/02 | (2006.01) |
| A61Q 5/12 | (2006.01) |

(52) U.S. Cl.
CPC .............. *A61K 8/416* (2013.01); *A61K 8/042* (2013.01); *A61K 8/342* (2013.01); *A61K 8/345* (2013.01); *A61K 8/361* (2013.01); *A61Q 5/002* (2013.01); *A61Q 5/02* (2013.01); *A61Q 5/12* (2013.01); *A61K 2800/591* (2013.01); *A61K 2800/805* (2013.01)

(58) Field of Classification Search
CPC . A61Q 5/12; A61Q 5/00; A61K 8/416; A61K 8/34; A61K 8/042
See application file for complete search history.

(56) References Cited

U.S. PATENT DOCUMENTS

| | | | | |
|---|---|---|---|---|
| 4,673,568 | A * | 6/1987 | Grollier | A61K 8/65 424/70.28 |
| 6,979,439 | B1 * | 12/2005 | Sakai | A61K 8/342 424/70.8 |
| 2007/0172441 | A1 | 7/2007 | Takeda et al. | |
| 2008/0311067 | A1 | 12/2008 | Murray et al. | |
| 2013/0164244 | A1 * | 6/2013 | Molenda | A61Q 5/12 424/70.13 |
| 2017/0273892 | A1 * | 9/2017 | Cox | A61Q 5/12 |

FOREIGN PATENT DOCUMENTS

| | | | | |
|---|---|---|---|---|
| EP | 2417961 A1 | 2/2012 | | |
| WO | WO-0117490 A1 * | 3/2001 | | A61K 8/39 |

OTHER PUBLICATIONS

Preliminary Search Report and Written Opinion issued on Apr. 9, 2021 for corresponding French Application No. 2007471.

* cited by examiner

*Primary Examiner* — Robert T. Crow
*Assistant Examiner* — John P Nguyen
(74) *Attorney, Agent, or Firm* — POLSINELLI PC

(57) ABSTRACT

Aspects of the disclosure relate to hair treatment compositions including about 0.1 to about 10 wt. % of a cationic surfactant; about 0.1 to about 10 wt. % of a fatty acid having a carbon chain of 12 or more carbons; about 0.1 to about 20 wt. % of a fatty alcohol; and about 50 wt. % or more of water, wherein all weight percentages are based on the total weight of the hair treatment composition. Additionally, the hair treatment compositions are formulated to have a molar ratio of the total amount of cationic surfactant to the total amount of fatty acid is about 1:0.8 to about 1:3 and a pH of about 2.5 to about 5.5. The disclosure also relates to methods for applying such hair treatment compositions.

4 Claims, 4 Drawing Sheets

HAIR TREATMENT COMPOSITIONS

CROSS-REFERENCE TO RELATED APPLICATIONS

This application claims benefit of U.S. Provisional Application Ser. No. 63/032,025, filed May 29, 2020, and benefit of French Application Serial No. FR 2007471, filed on Jul. 16, 2020, which are incorporated herein by reference in their entirety.

FIELD OF THE DISCLOSURE

The present disclosure relates to hair treatment compositions, and methods for applying and conditioning hair with such hair treatment compositions.

BACKGROUND OF THE DISCLOSURE

Many individuals suffer from dry and damaged hair. Dryness and damage can occur due to several factors including weather exposure, mechanical treatments (e.g. brushing hair), excessive treatments using chemicals, dying hair, heat styling, etc. In combination, using cleansing products that can be excessively stripping of hair's natural oils, can also lead to split ends, dull hair, and exacerbate dry hair. To mitigate the damage, oil treatments, conditioner, hair masks, and chemical treatments are commonly used.

The popularity and usage of oils for dry hair treatments has increased due to their effectiveness and simplicity. Commonly used oils include olive oil, mineral oil, avocado oil, apricot kernel oil, rice bran oil, and coconut oil. However, one problem is that effects are not usually seen after more than several hours (e.g. 8 hours) of treatment and several treatments are usually required, making it time consuming and labor intensive.

Individuals desire a treatment for hair or damaged hair that is not time consuming and labor intensive to use. A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits.

However, there is still a need for providing improved hair manageability and conditioning.

SUMMARY OF THE DISCLOSURE

Aspects of the present disclosure relate to hair treatment compositions for conditioning hair. The inventors discovered that hair treatment compositions may be formulated to have lamellar gel networks that are responsive to changes in the pH of the hair treatment compositions. For instance, changes in the pH of the hair treatment composition may result in precipitation of certain ingredients from the lamellar gel network. Without being limited to any specific theory, it is believed that increasing the pH of hair treatment composition of the instant disclosure above the pKa of the fatty acids, e.g., by the addition of extraneous water to dilute the composition, may destabilize the lamellar gel network, which promotes deposition of the certain ingredients (e.g., ingredients for conditioning hair) onto a user's hair.

The hair treatment compositions of the present disclosure typically include:
(a) about 0.1 to about 10 wt. % of a cationic surfactant;
(b) about 0.1 to about 10 wt. % of a fatty acid having a carbon chain of 12 or more carbons;
    wherein a molar ratio of the total amount of cationic surfactant to the total amount of fatty acid is 1:0.5 to 1:3,
(c) about 0.1 to about 20 wt. % of a fatty alcohol; and
(d) about 50 wt. % or more of water,
    wherein the hair treatment composition has a pH of 2.5 to 5.5, and all weight percentages are based on the total weight of the hair treatment composition.

The hair treatment composition may comprise a lamellar gel network. In some instances, the pH of the hair treatment composition is 3.5 to 5. The hair treatment composition may, optionally, be formulated such that the pH of the hair treatment composition is lower than the pKa of the fatty acid (e.g., before dilution by the addition of extraneous water).

The hair treatment composition may include a cationic surfactant that has a carbon chain that is within 10 carbon atoms of the length of the carbon chain of the fatty acid. Suitable cationic surfactants include cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, or mixtures thereof.

The fatty acid may have a carbon chain of 12 to 22 carbons. For example, the fatty acid may be chosen from lauric acid, myristic acid, palmitic acid, stearic acid, oleic acid, linoleic acid, ricinoleic acid, arachidic acid, behenic acid, and a mixture thereof. The hair treatment compositions may comprise at least two fatty acids, such as stearic acid and palmitic acid. The hair treatment compositions may comprise at least three fatty acids, such as myristic acid, palmitic acid, and stearic acid.

Non-limiting examples of suitable fatty alcohols include, but are not limited to, decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, or myricyl alcohol, or a mixture thereof.

The hair treatment composition may have about 0.1 to about 10 wt. % of a silicone. The silicone may be chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), dimethicone copolyols, dimethicone copolyol esters, dimethicone copolyol quaternium nitrogen containing compounds, dimethicone copolyol phosphate esters, silicone quaternium-18, and a mixture thereof.

Additionally or alternatively, the hair treatment composition may include about 0.01 to about 5 wt. % of one or more polymers chosen from polysaccharides, polyamines, acrylate polymers, polyurethanes, or a combination thereof.

The hair treatment composition may have about 0.01 to about 10 wt. % of a fatty compound other than fatty alcohols and fatty acids having a carbon chain of 12 or more carbons. The fatty compound other than fatty alcohols and fatty acids having a carbon chain of 12 or more carbons may be an oil chosen from triglycerides, esters, ethers, hydrocarbon, and a mixture thereof. In some instances, the fatty compound other than fatty alcohols and fatty acids having a carbon chain of 12 or more carbons is chosen from coconut oil, soybean oil, rapeseed oil, cottonseed oil, olive oil, palm oil, peanut oil, avocado oil, hazel nut oil, grapeseed oil, colza oil, cade oil, peach kernel oil, coffee bean oil, jojoba oil, caprylic/capric triglyceride, isopropyl myristate, PPG-3 myristyl ether, isopropyl palmitate, dibutyl adipate, propyleneglycol dicaprylate/dicaprate, cocoglyceride, cetearyl isononanoate, isopropyl myristate, isodecyl neopentanoate, tridecyl neopentanoate, $C_{12-15}$ alkyl benzoate, isopropyl lauroyl sarsosinate, phenethyl benzoate, $C_8$-$C_{19}$ alkanes, mineral oil, squalane, and a mixture thereof.

About 0.01 to about 5 wt. % of a polyol may be incorporated in the hair treatment composition. In some cases, the polyol is chosen from glycerin, diglycerin, glycol, and a mixture thereof. The polyol may be a glycol chosen from ethylene glycol, propylene glycol, butylene glycol, hexylene glycol, pentylene glycol, diethylene glycol, dipropylene glycol, 1,3 propanediol, 1,4-butanediol, 1,5-pentanediol, hexane-1,6-diol, polyethylene glycols, and a mixture thereof.

Methods for hair treatment according to the present disclosure typically include:

(I) applying a hair treatment composition, the hair treatment composition comprising:
  (a) about 0.1 to about 10 wt. % of a cationic surfactant;
  (b) about 0.1 to about 10 wt. % of a fatty acid having a carbon chain of 12 or more carbons;
    wherein a molar ratio of the total amount of cationic surfactant to the total amount of fatty acid is 1:1.05 to 1:3,
  (c) about 0.1 to about 20 wt. % of a fatty alcohol; and
  (d) about 50 wt. % or more of water,
    wherein the hair treatment composition has a pH of 2.5 to 5.5, and all weight percentages are based on the total weight of the hair treatment composition, and
(II) rinsing the hair treatment composition from the hair.

BRIEF DESCRIPTION OF THE DRAWING

Implementation of the present technology will now be described, by way of example only, with reference to the attached figure, wherein.

Figure 1A:
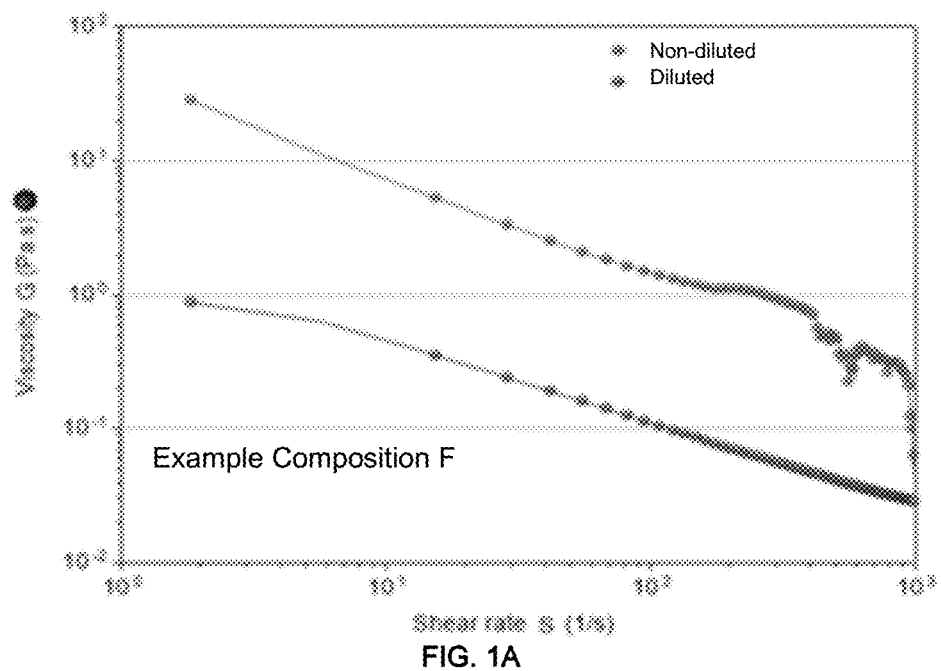
FIGS. 1A-1D are graphs of the viscosity as a function of shear for comparative compositions and example compositions in accordance with aspects of the disclosure.

It should be understood that the various aspects are not limited to the arrangements and instrumentality shown in the drawings.

DETAILED DESCRIPTION OF THE DISCLOSURE

Aspects of the present disclosure relate to hair treatment compositions. The hair treatment compositions may condition the hair, improve the hair's visual appearance, and/or strengthen the hair. The hair treatment compositions disclosed herein may be formulated to have a lamellar gel network that changes under certain conditions. For example, the hair treatment compositions may be formulated with specific ingredients in certain ratios such that the lamellar gel network is responsive (e.g., changes due to) to an increase in the pH, which promotes precipitation of ingredients for conditioning hair (e.g., emollients, silicones, certain fatty compounds). In at least one embodiment, the hair treatment composition has a pH that is less than the pKa of the fatty acids, such that increasing the pH of the hair treatment composition (e.g., by diluting the hair treatment composition with extraneous water) above the pKa of the fatty acid changes the lamellar gel network (e.g., by destabilizing the lamellar network) to promote precipitation and deposition of certain ingredients onto a user's hair. The inventor's discovered the hair treatment compositions provide improved disposition of certain desired ingredients onto the hair and provide improved hair attributes.

The pH of the hair treatment composition typically is 2.5 to 5.5. For example, the pH of the hair treatment composition may be from 2.5 to about 5.25, 2.5 to about 5, 2.5 to about 4.75, 2.5 to about 4.5, 2.5 to about 4.25, 2.5 to about 4, 2.5 to about 3.75, 2.5 to about 3.5, 2.5 to about 3.25, 2.5 to about 3; about 2.75 to 5.5, about 2.75 to about 5.25, about 2.75 to about 5, about 2.75 to about 4.75, about 2.75 to about 4.5, about 2.75 to about 4.25, about 2.75 to about 4, about 2.75 to about 3.75, about 2.75 to about 3.5; about 3 to 5.5, about 3 to about 5.25, about 3 to about 5, about 3 to about 4.75, about 3 to about 4.5, about 3 to about 4.25, about 3 to about 4, about 3 to about 3.75; about 3.25 to 5.5, about 3.25 to about 5.25, about 3.25 to about 5, about 3.25 to about 4.75, about 3.25 to about 4.5, about 3.25 to about 4.25, about 3.25 to about 4; about 3.5 to 5.5, about 3.5 to about 5.25, about 3.5 to about 5, about 3.5 to about 4.75, about 3.5 to about 4.5, about 3.5 to about 4.25; about 3.75 to 5.5, about 3.75 to about 5.25, about 3.75 to about 5, about 3.75 to about 4.75, about 3.75 to about 4.5; about 4 to 5.5, about 4 to about 5.25, about 4 to about 5, about 4 to about 4.75; about 4.25 to 5.5, about 4.25 to about 5.25, about 4.25 to about 5; about 4.25 to about 5.25, about 4.25 to about 5, about 4 to about 4.75; about 4.25 to about 5.25, or about 4.25 to about 5, ranges and subranges therebetween. The hair treatment composition may be formulated such that the pH of the hair treatment composition is lower than the pKa of the fatty acid (e.g., before dilution by the addition of extraneous water).

The hair treatment composition may be formulated such that the carbon chain of the cationic surfactant has a length that is within 10 carbon atoms of the length of the carbon chain of the fatty acid. In other words, the cationic surfactant and the fatty acid may be chosen such that the length of the carbon chain of the cationic surfactant is not greater than the length of the carbon chain of the fatty acid by 10 carbon atoms and also is not less than the length of the carbon chain of the same fatty acid by 10 carbon atoms. For example, the difference in the length of the carbon chain of the cationic surfactant and the length of the carbon chain of the fatty acid may be 10 carbon atoms or less, 9 carbon atoms or less, 8 carbon atoms or less, 7 carbon atoms or less, 6 carbon atoms or less, 5 carbon atoms or less, or 4 carbon atoms or less. In some instances, the cationic surfactant and the fatty acid may be chosen such that the difference in the length of the carbon chain of the cationic surfactant and the length of the carbon chain is between 0 and 10, 0 and 8, 0 and 6, 0 and 5, 0 and 4, 0 and 3, 1 and 10, 1 and 8, 1 and 6, 1 and 5, 1 and 4, 1 and 3, inclusive of the end points, including all ranges and subranges thereof.

The molar ratio of the total amount of cationic surfactant(s) to the total amount of fatty acid(s) for the hair treatment composition may be about 1:0.5 to about 3. For example, in some instances, the molar ratio of the total amount of cationic surfactant(s) to the total amount of fatty acid(s) is from about 1:0.5 to about 3, about 1:0.8 to about 3 about 1:0.85 to about 3, about 1:0.9 to about 3, about 1:0.95 to about 3, about 1:1 to about 3, about 1:1.05 to about 3, about 1:1.1 to about 3, about 1:1.15 to about 3, about 1:1.2 to about 3, about 1:1.25 to about 3, about 1:1.3 to about 3; about 1:0.8 to about 2.1, about 1:0.85 to about 2.1, about 1:0.9 to about 2.1, about 1:0.95 to about 2.1, about 1:1 to about 2.1, about 1:1.05 to about 2.1, about 1:1.1 to about 2.1, about 1:1.15 to about 2.1, about 1:1.2 to about 2.1, about 1:1.25 to about 2.1, about 1:1.3 to about 2.1; about 1:0.8 to about 1.6, about 1:0.85 to about 1.6, about 1:0.9 to about 1.6, about 1:0.95 to about 1.6, about 1:1 to about 1.6, about 1:1.05 to about 1.6, about 1:1.1 to about 1.6, about 1:1.15 to about 1.6, about 1:1.2 to about 1.6, about 1:1.25 to about 1.6, about 1:1.3 to about 1.6; about 1:0.8 to about 1.5, about 1:0.85 to about 1.5, about 1:0.9 to about 1.5, about 1:0.95 to about 1.5, about 1:1 to about 1.5, about 1:1.05 to about 1.5, about 1:1.1 to about 1.5, about 1:1.15 to about 1.5, about 1:1.2 to about 1.5, about 1:1.25 to about 1.5, about 1:1.3 to about 1.5; about 1:0.8 to about 1.45, about 1:0.85 to about 1.45, about 1:0.9 to about 1.45, about 1:0.95 to about 1.45, about 1:1 to about 1.45, about 1:1.05 to about 1.45, about 1:1.1 to about 1.45, about 1:1.15 to about 1.45, about 1:1.2 to about 1.45, about 1:1.25 to about 1.45; about 1:0.8 to about 1.4, about 1:0.85 to about 1.4, about 1:0.9 to about 1.4, about 1:0.95 to about 1.4, about 1:1 to about 1.4, about 1:1.05 to about 1.4, about 1:1.1 to about 1.4, about 1:1.15 to about 1.4, about 1:1.2 to about 1.4; about 1:0.8 to about 1.35, about 1:0.85 to about 1.35, about 1:0.9 to about 1.35, about 1:0.95 to about 1.35, about 1:1 to about 1.35, about 1:1.05 to about 1.35, about 1:1.1 to about 1.35, about 1:1.15 to about 1.35; about 1:0.8 to about 1.3, about 1:0.85 to about 1.3, about 1:0.9 to about 1.3, about 1:0.95 to about 1.3, about 1:1 to about 1.3, about 1:1.05 to about 1.3, about 1:1.1 to about 1.3, or about 1:1.15 to about 1.3, including ranges and subranges thereof.

In some instances, the hair treatment composition is free or substantially free of non-ionic polymers of alkylene oxide. In some instances, the hair treatment composition may have an amount of nonionic polymers of alkylene oxide that is less than 6 wt. %, preferably less than 5 wt. %, preferably less than 4 wt. %, preferably less than 3 wt. %, preferably less than 2 wt. %, preferably less than 1 wt. %, preferably less than 0.5 wt. %, and/or preferably less than 0.1 wt. %, based on the total weight of the hair treatment composition. In at least embodiment, the hair treatment composition has essentially 0 wt. % or 0 wt. % of nonionic polymers of alkylene oxide, based on the total weight of the hair treatment composition.

In some instances, the hair treatment composition is free or substantially free of PEGylated compounds. In some instances, the hair treatment composition may have an amount of PEGylated compounds that is less than 6 wt. %, preferably less than 5 wt. %, preferably less than 4 wt. %, preferably less than 3 wt. %, preferably less than 2 wt. %, preferably less than 1 wt. %, preferably less than 0.5 wt. %, and/or preferably less than 0.1 wt. %, based on the total weight of the hair treatment composition. In at least embodiment, the hair treatment composition has essentially 0 wt. % or 0 wt. % of PEGylated compounds, based on the total weight of the hair treatment composition.

In some instances, the hair treatment composition is free or substantially free of polypropylene glycol (PPG) compounds. In some instances, the hair treatment composition may have an amount of polypropylene glycol (PPG) that is less than 6 wt. %, preferably less than 5 wt. %, preferably less than 4 wt. %, preferably less than 3 wt. %, preferably less than 2 wt. %, preferably less than 1 wt. %, preferably less than 0.5 wt. %, and/or preferably less than 0.1 wt. %, based on the total weight of the hair treatment composition. In at least embodiment, the hair treatment composition has essentially 0 wt. % or 0 wt. % of polypropylene glycol (PPG), based on the total weight of the hair treatment composition.

Suitable components, such as those listed below, may be included or excluded from the formulations for the hair treatment compositions depending on the specific combination of other components, the form of the hair treatment compositions, and/or the use of the formulation (e.g., a lotion, gel, cream, spray, etc.).

Cationic Surfactant(s)

The hair treatment composition includes a cationic surfactant(s). The amount of cationic surfactant(s) may be from about 0.1 to about 10 wt. % of the total weight of the hair treatment composition. In some instances, the cationic surfactant(s) are in an amount ranging from about 0.1 to about 10 wt. %, about 0.1 to about 8 wt. %, about 0.1 to about 6 wt. %, about 0.1 to about 4 wt. %, about 0.1 to about 3 wt. %; about 0.2 to about 10 wt. %, about 0.2 to about 8 wt. %, about 0.2 to about 6 wt. %, about 0.2 to about 4 wt. %, about 0.2 to about 3 wt. %; about 0.5 to about 10 wt. %, about 0.5 to about 8 wt. %, about 0.5 to about 6 wt. %, about 0.5 to about 4 wt. %, about 0.5 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, including ranges and sub-ranges therebetween, based on the total weight of the hair treatment composition.

The hair treatment composition may include a cationic surfactant that has a carbon chain that is within 10 carbon atoms of the length of the carbon chain of the fatty acid. Suitable cationic surfactants include cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, or mixtures thereof.

Additional, non-limiting examples of cationic surfactants include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and mixtures thereof.

The cationic surfactant(s) may also be chosen from optionally polyoxyalkylenated, primary, secondary or tertiary fatty amines, or salts thereof, and quaternary ammonium salts, and mixtures thereof. In some cases it is useful to use salts such as chloride salts of the quaternary ammonium compounds.

The fatty amines generally comprise at least one $C_8$-$C_{30}$ hydrocarbon-based chain. For example, quaternary ammonium salts, which may be incorporated in certain instances, include those corresponding to the following general formula:

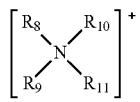

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_3$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having a structure in accordance with the above general formula (III), those that are preferred are, on the one hand, tetraalkylammonium salts, for instance dialkyldimethylammonium or alkyltrimethylammonium salts in which the alkyl group contains approximately from 12 to 22 carbon atoms, such as behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Examples of quaternary ammonium salt of imidazoline, which may be incorporated in certain instances, include those having a structure according to the general formula provided below:

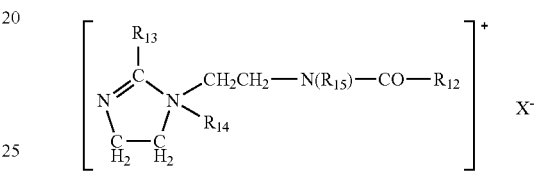

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo.

Examples of quaternary diammonium or triammonium salt, which may be incorporated in certain instances, include those having a structure in accordance with the following general formula:

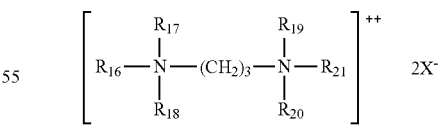

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group ($R_{16a}$)($R_{17a}$)($R_{18a}$)N—(CH$_2$)$_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and $X^-$ is an anion chosen from the group of halides, acetates, phosphates, nitrates and methyl sulfates. Such compounds are, for example, FINQUAT CT-P, sold by the company FINTEX (Quaternium 89), and FINQUAT CT, sold by the company FINETEX (Quaternium 75).

Examples of cationic/cationizable surfactants, which may be incorporated in certain instances, include those having a structure in accordance with the general formula provided below:

R4-A-R5-B wherein R4 is a saturated or unsaturated, straight or branched alkyl chain with 8 to 24 C atoms, R5 is a straight or branched alkyl chain with 1 to 4 C atoms, A is selected from:

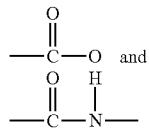

and B is selected from:

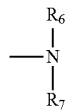

wherein $R_6$ and $R_7$ are the same or different and are H or an alkyl chain with 1 to 4 C atoms, hydroxyl alkyl chain with 1 to 4 C atoms and di hydroxyl alkyl chain with 2 to 4 C atoms,

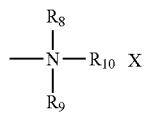

$R_3$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24 C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, stearamidopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines, preferably, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citric acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

In an embodiment, hair treatment composition may be formulated with a cationic surfactant chosen from behentrimonium chloride, cetrimonium chloride, behentrimonium methosulfate, or mixtures thereof.

The hair treatment composition may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

Fatty Acid(s)

The hair treatment composition includes fatty acids in an amount that may vary, but typically ranges from about 0.1 to about 10 wt. %, based on the total weight of the hair treatment composition. For example, the amount of fatty acids(s) present in the hair treatment composition may range from about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, %, about 0.5 to about 3 wt. %, about 0.5 to about 2 wt. %; about 0.5 to about 10 wt. %, about 0.5 to about 9 wt. %, about 0.5 to about 8 wt. %, about 0.6 to about 7 wt. %, about 0.6 to about 6 wt. %, about 0.6 to about 5 wt. %, about 0.6 to about 4 wt. %, about 0.6 to about 3 wt. %, about 0.6 to about 2 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, or about 1 to about 3 wt. %, or about 1 to about 2 wt. %, including all ranges and sub-ranges therebetween, based on the total weight of the hair treatment composition.

The fatty acids may be straight or branched chain acids and/or may be saturated or unsaturated. The fatty acid may have 8 to 30 carbons, e.g., 8 to 25, 8 to 22, 8 to 20, 8 to 18, or 8 to 16 carbons. In some cases, the fatty acid has 12 to 30, 12 to 25, 12 to 22, 12 to 20, 12 to 18 carbons. In further cases, the fatty acids may comprise $C_8$-$C_{22}$ or $C_{14}$-$C_{22}$ fatty groups, which may be saturated or unsaturated linear alkyl chain containing. The fatty acids may have fatty groups chosen from stearate, isostearate, linoleate, oleate, behenate, arachidonate, palmitate, myristate, laurate, caprate, isostearyl, stearyl, linoleyl, oleyl, behenyl, myristyl, lauryl or capryl chains, and mixtures thereof.

Non-limiting examples of fatty acids include monaacids, diacids, triacids, and other multiple acids as well as salts of these fatty acids. For example, the fatty acid may optionally include or be chosen from lauric acid, myristic acid, palmitic acid, stearic acid, behenic acid, arichidonic acid, oleic acid, isostearic acid, sebacic acid, and a mixture thereof. The fatty acids may be selected from the group consisting of palmitic acid, myristic acid, stearic acid, and a mixture thereof. In some instances, the fatty acid may be chosen from fatty acids, fatty acid derivatives and/or alkoxylated fatty acids.

Non-limiting examples of polyglycerol esters of fatty acids include those of the following formula:

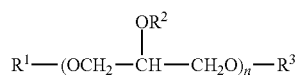

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Non-limiting examples fatty acid alkanolamides include fatty acid monoalkanolamides, fatty acid dialkanolamides, or fatty acid isoalkanolamides. Fatty acid alkanolamides may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Fatty Alcohol(s)

The hair treatment compositions include an amount of fatty alcohol(s) typically in the range of about 0.1 to about 20 wt. %, based on the total weight of the hair treatment composition. For example, the amount of fatty alcohol(s) present in the hair treatment composition may range from about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %; about 1.5 to about 15 wt. %, about 1.5 to about 10 wt. %, about 1.5 to about 8 wt. %, about 1.5 to about 6 wt. %, about 1.5 to about 5 wt. %, about 1.5 to about 4 wt. %; about 2 to about 20 wt. %, about 2 to about 15 wt. %, about 2 to about 10 wt. %, about 2 to about 8 wt. %, about 2 to about 6 wt. %, about 2 to about 5 wt. %, about 2 to about 4 wt. %; about 2.5 to about 20 wt. %, about 2.5 to about 15 wt. %, about 2.5 to about 10 wt. %, about 2.5 to about 8 wt. %, about 2.5 to about 6 wt. %, about 2.5 to about 5 wt. %, or about 2.5 to about 4 wt. %, including all ranges and sub-ranges therebetween, based on the total weight of the hair treatment composition.

Preferably, the fatty alcohols have a carbon chain of 12 or more carbons. Non-limiting examples of suitable fatty alcohols include, but are not limited to, decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, or myricyl alcohol, or a mixture thereof.

More generally, the fatty alcohols may be liquid at 25° C., 1 atm, or may even be solid. They may even be glycerolated and/or oxyalkylenated, and may include from 8 to 30 carbon atoms. They may be saturated or unsaturated. For example, the fatty alcohols may be chosen from those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of myristyl alcohol, cetyl alcohol, stearyl alcohol, isostearyl alcohol, oleyl alcohol, isotridecyl alcohol, and a mixture thereof.

The saturated liquid fatty alcohols may be branched. They can optionally comprise, in their structure, at least one aromatic or non-aromatic ring, but are preferably acyclic. Non-limiting examples of liquid saturated fatty alcohols include octyldodecanol, isostearyl alcohol, and 2-hexyldecanol.

The unsaturated liquid fatty alcohols may include in their structure at least one double or triple bond and, in some instances, one or more double bonds. When several double bonds are present, there are preferably 2 or 3 of them and they can be conjugated or non-conjugated. These unsaturated fatty alcohols can be linear or branched. They can optionally include in their structure at least one aromatic or non-aromatic ring but they are preferably acyclic. Among liquid unsaturated fatty alcohols, oleyl alcohol, linoleyl alcohol, linolenyl alcohol and undecylenyl alcohol can be cited.

Non-limiting examples of solid fatty alcohols include linear or branched, saturated or unsaturated alcohols containing from 8 to 30 carbon atoms, for example, myristyl alcohol, cetyl alcohol, stearyl alcohol, and cetearyl alcohol.

Non-limiting examples of high melting point fatty compounds include fatty alcohols such as, for example, myristyl alcohol (having a melting point of about 38° C.), cetyl alcohol (having a melting point of about 56° C.), stearyl alcohol (having a melting point of about 58-59° C.), behenyl alcohol (having a melting point of about 71° C.), and mixtures thereof. These compounds are known to have the above melting points. However, they often have lower melting points when supplied, since such supplied products are often mixtures of fatty alcohols having alkyl chain length distribution in which the main alkyl chain is cetyl, stearyl or behenyl group. In the present disclosure, more preferred fatty alcohols are myristyl alcohol, cetyl alcohol, stearyl alcohol and mixtures thereof.

Silicone(s)

The hair treatment composition includes silicone(s) typically in an amount ranging from about 0.1 to about 10 wt. %, based on the total weight of the hair treatment composition. For example, the amount of silicone(s) present in the hair treatment composition may range from about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %; about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; about 1.5 to about 10 wt. %, about 1.5 to about 8 wt. %, about 1.5 to about 6 wt. %, about 1.5 to about 5 wt. %, about 1.5 to about 4 wt. %, about 1.5 to about 3 wt. %; about 2 to about 10 wt. %, about 2 to about 8 wt. %, about 2 to about 6 wt. %, about 2 to about 5 wt. %, about 2 to about 4 wt. %, about 2 to about 3 wt. %; about 2.5 to about 10 wt. %, about 2.5 to about 8 wt. %, about 2.5 to about 6 wt. %, about 2.5 to about 5 wt. %, about 2.5 to about 4 wt. %, including all ranges and sub-ranges therebetween, based on the total weight of the hair treatment composition.

The silicone may be chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), dimethicone copolyols, dimethicone copolyol esters, dimethicone copolyol quaternium nitrogen containing compounds, dimethicone copolyol phosphate esters, silicone quaternium-18, and a mixture thereof.

The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of silicones include amine-functionalized silicones (e.g., amodimethicone), dimethicone, bis-aminopropyl dimethicone, trimethyl silylamodimethicone, dimethicone copolyols, etc. The hair treatment composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicones may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

The silicone(s) may, optionally, include or be chosen from a siloxane with a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

In some cases, the silicones, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

In some instances, an amino-functionalized silicones is selected from compounds having the following formula:

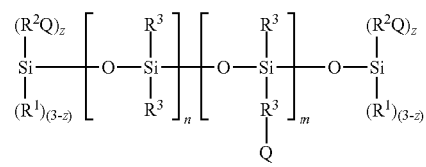

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $-NR^4_2$ and $-NR^4(CH_2)_xNR^4_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydroxyl. Preferred $R^2$ divalent alkylene radicals include trimethylene, tetramethylene, pentamethylene, $-CH_2CH(CH_3)CH_2-$ and $-CH_2CH_2CH(CH_3)CH_2-$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicine has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds of the following formula:

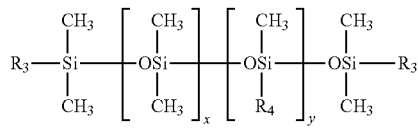

wherein $R_3$ is hydroxyl or $OR_5$, $R_5$ is a $C_1$ to $C_4$ alkyl group, $R_4$ is a group with structure according to the following formula:

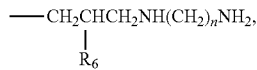

$R_6$ is a $C_1$ to $C_4$ alkyl, n is a 1 to 4, x is the same as "n" described above, and y is the same as "m" described above.

The silicone may be a polysiloxane corresponding to the following formula:

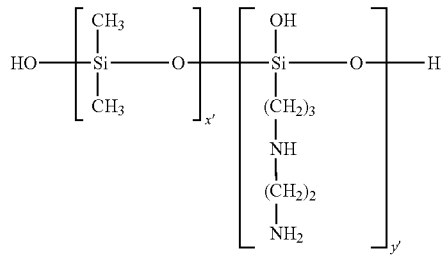

in which x' and y' are integers such that the weight-average molecular weight (Mw) is comprised between about 5000 and 500 000;

b) amino silicones corresponding to following formula:

in which:
G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —CqH2qL in which q is a number ranging from 2 to 8 and L is an optionally quaternized amino group chosen from the following groups:
—NR"-Q-N(R")2
—N(R")2
—N+(R")3A-
—N+H(R")2A-
—N+H2(R") A-
—N(R")-Q-N+R"H2A-
—NR"-Q-N+(R")2H A-
—NR"-Q-N+(R")3A-, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A-represents a cosmetically acceptable ion, in particular a halide such as fluoride, chloride, bromide or iodide.

Another group of amino silicones corresponding to this definition is represented by silicones having the following formula:

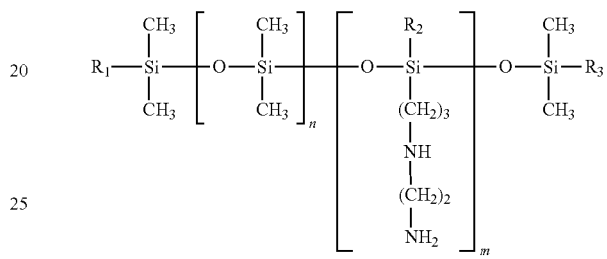

in which:
m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical. The hydroxy/alkoxy mole ratio ranges preferably from 0.2:1 to 0.4:1 and preferably from 0.25:1 to 0.35:1 and more particularly equals 0.3:1. The weight-average molecular weight (Mw) of the silicone ranges preferably from 2,000 to 1,000,000, more particularly from 3,500 to 200,000.

Another group of amino silicones corresponding to this definition is represented by the following formula:

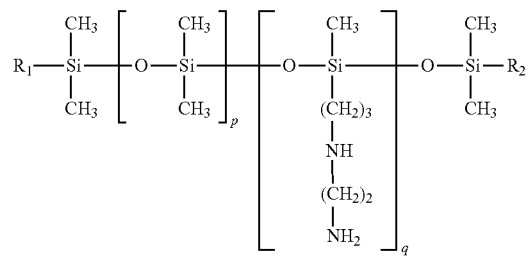

in which:
p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which may be the same or different, represent a hydroxy or $C_1$-$C_4$ alkoxy radical, where at least one of the radicals $R_1$ or $R_2$ denotes an alkoxy radical.

The alkoxy radical is preferably a methoxy radical. The hydroxy/alkoxy mole ratio ranges generally from 1:0.8 to 1:1.1 and preferably from 1:0.9 to 1:1 and more particularly equals 1:0.95.

Another group of amino silicones is represented by the following formula:

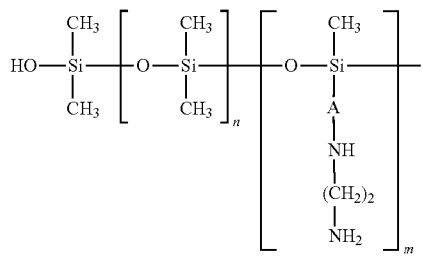

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

Another group of amino silicones is represented by the following formula:

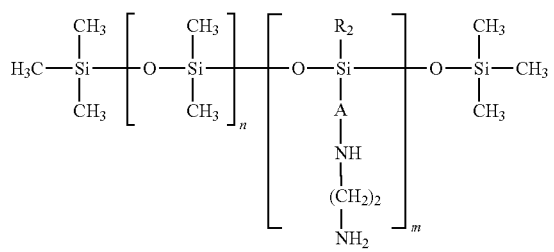

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

Another group of amino silicones is represented by the following formula:

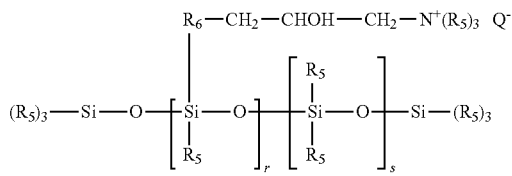

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q– is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in U.S. Pat. No. 4,185,087.

A group of quaternary ammonium silicones is represented by the following formula:

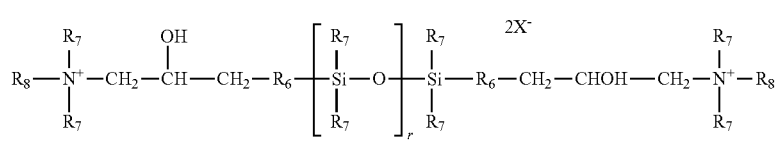

in which:
$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_8$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_B$—$NHCOR_7$ radical;

X— is an anion such as a halide ion, in particular chloride, or an organic acid salt (for example acetate);

r represents a mean statistical value from 2 to 200 and in particular from 5 to 100. These silicones are described, for example, in patent application EP-A 0530974.

A group of quaternary ammonium silicones is represented by the following formula:

$$H_2N\text{---}(C_mH_{2m})\text{---}NH\text{---}(C_mH_{2n})\text{---}Si\left[\text{---}O\left[\begin{array}{c}R_1\\|\\Si\\|\\R_2\end{array}\text{---}O\right]_x\begin{array}{c}R_3\\|\\Si\\|\\R_4\end{array}\text{---}R_5\right]_3 \quad (J)$$

in which:
$R_1$, $R_2$, $R_3$ and $R_4$, which may be identical or different, denote a $C_1$-$C_4$ alkyl radical or a phenyl group;
$R_5$ denotes a $C_1$-$C_4$ alkyl radical or a hydroxyl group;
n is an integer ranging from 1 to 5;
m is an integer ranging from 1 to 5;
and in which x is chosen such that the amine number is between 0.01 and 1 meq/g;
multiblock polyoxyalkylenated amino silicones, of type (AB)n, A being a polysiloxane block and B being a polyoxyalkylenated block containing at least one amine group.

Said silicones are preferably constituted of repeating units having the following general formulae:

[—(SiMe$_2$O)xSiMe$_2$-R—N(R")—R'—O(C$_2$H$_4$O)$_a$
(C$_3$H$_6$O)$_b$—R'—N(H)—R—]

or alternatively

[—(SiMe$_2$O)xSiMe$_2$-R—N(R")—R'—O(C$_2$H$_4$O)$_a$
(C$_3$H$_6$O)$b$-]

in which:
a is an integer greater than or equal to 1, preferably ranging from 5 to 200, more particularly ranging from 10 to 100;
b is an integer comprised between 0 and 200, preferably ranging from 4 to 100, more particularly between from 5 and 30;
x is an integer ranging from 1 to 10 000, more particularly from 10 to 5000;
R" is a hydrogen atom or a methyl;
R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —CH$_2$CH$_2$CH$_2$OCH(OH)CH$_2$— radical; preferentially R denotes a —CH$_2$CH$_2$CH$_2$OCH(OH)CH$_2$— radical;
R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —CH$_2$CH$_2$CH$_2$OCH(OH)CH$_2$— radical; preferentially R' denotes —CH(CH$_3$)—CH$_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2. The weight-average molecular weight (Mw) of the silicone oil is preferably comprised between 5000 and 1,000,000, more particularly between 10,000 and 200,000.

The silicone may be selected from those having at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof. In an embodiment, the one or more silicone oils of the present disclosure is a non-amino silicone oil such as a dimethicone.

Non-limiting examples of amino-functionalized silicones include bis-hydroxy/methoxy amodimethicones, bis-cetearyl amodimethicone, amodimethicone, bis($C_{13-15}$ alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is OCH$_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company. A non-limiting example of amodimethicone products containing amino silicones having structure (D) re sold by Wacker under the name BELSIL ADM 652, BELSIL ADM 4000 E, or BELSIL ADM LOG 1. A product containing amino silicones having structure (E) is sold by Wacker under the name FLUID WR 1300. Additionally or alternative, the weight-average molecular weight (Mw) of the silicone ranges preferably from 2,000 to 200,000, even more particularly 5,000 to 100,000 and more particularly from 10,000 to 50,000.

The silicone(s) in the hair treatment compositions of the instant disclosure can be included in a pure form (e.g., a non-emulsified form) or the form of a silicone emulsion comprising at least one silicone and at least one surfactants, for example, nonionic surfactants, cationic surfactants, amphoteric surfactants, anionic surfactants. The silicone emulsions can be nanoemulsions, microemulsions or macroemulsions. Suitable examples of nonionic surfactants are alkoxylated fatty alcohols or polyethylene glycol ethers of mixtures of C8-C30 fatty alcohols with an average of number of moles of ethylene oxide such as C11-15 Pareth-7, laureth-9, laureth-12, deceth-7, deceth-10, trideceth-6, trideceth-10, trideceth-12, or a mixture thereof. Suitable examples of amphoteric surfactants are cocamidopropyl betaine, coco-betaine, or a mixture thereof. Suitable examples of cationic surfactants are quaternary ammonium compounds such as behentrimonium chloride, cetrimoinium chloride, behentrimonium methosulfate, or a mixture thereof. Suitable examples of anionic surfactants are sulfate-based compounds such as further comprises up to 5 wt. % of a surfactant, for example, sodium (or ammonium) lauryl sulfate, sodium (or ammonium) laureth sulfate, or mixtures thereof.

Polymer(s)

The hair treatment composition may optionally include one or more polymers chosen from polysaccharides, polyamines, acrylate polymers, polyurethanes, or a combination thereof. The amount of polymers chosen from polysaccharides, polyamines, acrylate polymers, polyurethanes, or a combination thereof may vary, but typically is present in the hair treatment composition in amount from about 0.01 to about 5 wt. %. For example, the polymers chosen from polysaccharides, polyamines, acrylate polymers, polyurethanes, or a combination thereof may be present in an amount of about 0.01 to about 5 wt. %, about 0.01 to about 4 wt. %, about 0.01 to about 3 wt. %, about 0.01 to about 2 wt. %, about 0.01 to about 1 wt. %; about 0.05 to about 5 wt. %, about 0.05 to about 4 wt. %, about 0.05 to about 3 wt. %, about 0.05 to about 2 wt. %, about 0.05 to about 1 wt. %; about 0.1 to about 5 wt. %, about 0.1 to about 4 wt. %, about 0.1 to about 3 wt. %, about 0.1 to about 2 wt. %, about 0.1 to about 1 wt. %; about 0.5 to about 5 wt. %, about 0.5 to about 4 wt. %, about 0.5 to about 3 wt. %, about 0.5 to about 2 wt. %, about 0.5 to about 1 wt. %; about 1 to about 5 wt. %, about 1 to about 4 wt. %, about 1 to about 3 wt. %, or about 1 to about 2 wt. %, ranges and subranges therebetween, based on the total weight of the hair treatment composition.

Non-limiting examples of polymers that may be present in the hair treatment composition include, but are not limited to:

Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename NATROSOL CS Plus from Aqualon Corporation.

Other useful polysaccharides include scleroglucans comprising a linear chain of (1-3) linked glucose units with a (1-6) linked glucose every three units, a commercially available example of which is CLEAROGEL CS11 from Michel Mercier Products Inc.

Polyamines

The hair treatment compositions may include one or more polyamines. Examples of polyamines include the product POLYQUART H sold by COGNIS under the reference name polyethylene glycol (15) tallow polyamine in the CTFA dictionary. The polyamines may be polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine. Additionally or alternatively, polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Non-limiting examples of such derivatives include the adipic acid/epxoypropyl/diethylenetriamine.

The polyamines may be chosen from polyacrylamide polymers, such as non-ionic polyacrylamide polymers including substituted branched or unbranched polymers. Among these polyacrylamide polymers is the nonionic polymer given the CTFA designation polyacrylamide and isoparaffin and laureth-7, available under the Tradename SEPI-GEL 305 from Seppic Corporation. Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500W, SSSA100H, from Lipo Chemicals, Inc.

Acrylate Polymer(s)

The hair treatment compositions can optionally contain acrylate polymers useful as thickeners or gelling agents including both cationic and nonionic polymers. Non-limiting examples of acrylate polymers include acrylates/hydroxyesters acrylate copolymer, polyacrylate-2 crosspolymer, acrylates/C1-2 succinates/hydroxyacrylates copolymer, acrylic copolymer, acrylates/hydroxyesters acrylate copolymer, ammonium acrylates copolymer, styrene/acrylates copolymer, copolymer of methyl methacrylate butyl acrylate and methacrylic acid, styrene/acrylates/ammonium methacrylate copolymer, alkyl acrylate/styrene copolymer, acrylate/VA copolymer, polycarbamyl polyglycol ester and PVP/polycarbamyl polyglycol ester, and combinations thereof. The hair treatment composition may include crosslinked non-ionic polyacrylate polymers and crosslinked cationic polyacrylate polymers are those described in U.S. Pat. Nos. 5,100,660, 4,849,484, 4,835,206, 4,628,078 U.S. Pat. No.

4,599,379 and EP 228,868, which are all incorporated herein by reference in their entirety for all purposes.

Polyurethane(s)

The hair treatment compositions may include non-ionic polyether polyurethanes comprising, in their chain, both hydrophilic blocks, usually of polyoxyethylene nature, and hydrophobic blocks that may be aliphatic sequences alone and/or cycloaliphatic and/or aromatic sequences. Preferably, these polyether polyurethanes comprise at least two lipophilic hydrocarbon chains containing from 6 to 30 carbon atoms, separated by a hydrophilic block, the hydrocarbon chains possibly being pendant chains or chains at the end of the hydrophilic block. In particular, it is possible for one or more pendant chains to be provided. In addition, the polymer may comprise a hydrocarbon-based chain at one end or at both ends of a hydrophilic block.

The polyether polyurethanes may have multiple blocks, particularly in the form of triblocks. The hydrophobic blocks can be at each end of the chain (for example: triblock copolymer having a hydrophilic central block) or distributed both at the ends and in the chain (for example, multiblock copolymer). These same polymers can also be graft polymers or star polymers. The nonionic polyether polyurethanes with fatty chains may be triblock copolymers whose hydrophilic block is a polyoxyethylenated chain including from 50 to 1000 oxyethylene groups. The non-ionic polyether polyurethanes comprise a urethane linkage between the hydrophilic blocks. Also included among the non-ionic polyether polyurethanes comprising a hydrophobic chain are those in which the hydrophilic blocks are linked to the hydrophobic blocks via other chemical bonds.

Examples of potentially useful polyurethane film-forming polymers include, for example, polyurethane-32, polyurethane-34, polyurethane-35, polyurethane-48, and a mixture thereof.

Fatty Compound(s) Other than Fatty Alcohols and Fatty Acids Having a Carbon Chain of 12 or More Carbons The hair treatment compositions may optionally include one or more fatty compounds other than fatty alcohols and fatty acids having a carbon chain of 12 or more carbons. The amount of such fatty compounds, if present in the hair treatment composition, may range from about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.05 to about 10 wt. %, about 0.05 to about 8 wt. %, about 0.05 to about 6 wt. %, about 0.05 to about 5 wt. %, about 0.05 to about 4 wt. %, about 0.05 to about 3 wt. %, about 0.05 to about 2 wt. %, about 0.05 to about 1 wt. %; about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, ranges and subranges therebetween, based on the total weight of the hair treatment composition.

Suitable fatty compounds other than fatty compounds other than fatty alcohols and fatty acids having a carbon chain of 12 or more carbons may be chosen from oils, mineral oil, alkanes (paraffins), fatty acids having a carbon chain of 12 or less, fatty alcohol derivatives, fatty acid derivatives, esters of fatty alcohols, hydroxy-substituted fatty acids, waxes, triglyceride compounds, lanolin, and a mixture thereof.

The fatty compound other than fatty alcohols and fatty acids having a carbon chain of 12 or more carbons may be an oil chosen from triglycerides, esters, ethers, hydrocarbon, and a mixture thereof. In some instances, the fatty compound other than fatty alcohols and fatty acids having a carbon chain of 12 or more carbons is chosen from coconut oil, soybean oil, rapeseed oil, cottonseed oil, olive oil, palm oil, peanut oil, avocado oil, hazel nut oil, grapeseed oil, colza oil, cade oil, peach kernel oil, coffee bean oil, jojoba oil, caprylic/capric triglyceride, isopropyl myristate, PPG-3 myristyl ether, isopropyl palmitate, dibutyl adipate, propyleneglycol dicaprylate/dicaprate, cocoglyceride, cetearyl isononanoate, isopropyl myristate, isodecyl neopentanoate, tridecyl neopentanoate, $C_{12-15}$ alkyl benzoate, isopropyl lauroyl sarsosinate, phenethyl benzoate, $C_8$-$C_{19}$ alkanes, mineral oil, squalane, and a mixture thereof.

Further examples of fatty compounds other than fatty alcohols and fatty acids having a carbon chain of 12 or more carbons include fatty esters, glyceryl esters (glycerol esters), fatty esters, alkyl ethers of fatty alcohols, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof. Examples of fatty esters include fatty carbonate esters, glycerol fatty esters, sucrose fatty esters, sorbitan fatty ester, fatty acid esters, or mixtures thereof. Non-limiting examples of the fatty alcohol derivatives, and fatty acid derivatives are found in International Cosmetic Ingredient Dictionary, Sixteenth Edition, 2016, which are incorporated by reference herein in its entirety.

In some instances, the fatty compounds may include or be chosen from one or more oil(s). Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelargante; and triesters, such as glyceryl trioctanoate. Non-limiting examples of oils that may, optionally, be included in the hair treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

The fatty compounds other than fatty alcohols and fatty acids having a carbon chain of 12 or more carbons may function as an emollient. The emollient may be a polar emollient or a non-polar emollient. As used herein, "polar emollient" means any emollient having at least one polar moiety. The emollient may be one or both of high and medium polarity oil soluble emollients. Non-limiting examples of polar emollients include, but are not limited to, esters, polyol esters, and polyol ethers such as linear or branched chained polyglycerol esters and polyglycerol ethers. For example, the emollient be chosen from or comprise caprylic/capric triglyceride, isopropyl myristate, PPG-3 myristyl ether, isopropyl palmitate, dibutyl adipate, propyleneglycol dicaprylate/dicaprate, cocoglyceride, cetearyl isononanoate, isopropyl myristate, isodecyl neopentanoate, tridecyl neopentanoate, $C_{12-15}$ alkyl benzoate, isopropyl lauroyl sarsosinate, phenethyl benzoate, and mixtures thereof. Other examples of emollients include oil soluble emollients having high or medium polarity moieties.

The emollient may be a non-polar oil soluble emollients. "Non-polar emollient," as used herein, means any emollient possessing no permanent electric moments. Non-limiting examples of non-polar emollients may include, but are not limited to, non-polar hydrocarbon, such as esters, linear or branched, or chained hydrocarbons. For example, the emollients may be chosen from or include paraffins, isoparaffins, mineral oil, silicone oils, dimethicone, isohexadecane, isododecane, diethylhexyl cyclohexane, and mixtures thereof. In some instances, emollient comprises or is chosen from dicaprylyl ether, isododecane, hydrocarbon, dimethicone and mixtures thereof. In other cases, the emollient includes non-silicone oils and dimethicone. In yet further case, the emollient includes dimethicone with one or more additional non-polar emollients. Preferably, the emollient comprises or is chosen from isopropyl myristate and/or dicaprylyl carbonate.

Additionally or alternatively, certain emollients suitable for incorporating into the hair treatment composition may be categorized and chosen from the following groups: plant-based or vegetal oils, esters, ethers, paraffins and hydrocarbon-based oils.

Plant-Based or Vegetal Oils

Non-limiting examples of plant-based or vegetal oils include non-limiting example include plant-based or vegetal oils such as acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, *cannabis* oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, *eucalyptus* oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, *melaleuca*, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, *perilla* oil, pennyroyal oil, peppermint oil, petitgrain, pine oil, plum oil, ravensara, red cedar, roman chamomile, rose oil, rosehip oil, rosemary oil, rosewood oil, sandalwood oil, *sassafras* oil, savory oil, schisandra oil, spikenard, spruce, star anise oil, tangerine, tarragon oil, tea tree oil, thyme oil, *tsuga* oil, turmeric, valerian, vetiver oil, western red cedar, wintergreen, yarrow oil, ylang-ylang, and zedoary oil.

In some embodiments, the suitable vegetal oils for use in the leave-on hair care compositions of the present invention are selected from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, almond oil, babassu oil (Orbigyna Oleifera Seed Oil), jojoba oil, peanut oil, soybean oil, *Helianthus annuus* (sunflower) seed oil, and mixtures thereof.

In some cases, the leave-on hair care composition includes at least coconut oil.

In a preferred embodiment the suitable vegetal oil of the present invention is selected from coconut oil, which may be commercially available under various tradenames from different companies such as NEUTRESCA 51-25 from the company Aarhuskarl Shamn or REFINED COCONUT OIL—L from the company Aakkamani Private or AGRIPURE AP-20 from the company Cargill or EDIBLE COCONUT OIL N degrees 76 from the company Welch Holme and Clark.

Esters and Ethers

Suitable esters and ethers include polyol esters and polyol ethers such as linear or branched chained polyglycerol esters and polyglycerol ethers. Particularly suitable for use as the emmolients include caprylic/capric triglyceride, isopropyl alcohol, caprylic/capric glycerides, isopropyl myristate, PPG-3 myristyl ether, isopropyl palmitate, dibutyl adipate, propyleneglycol dicaprylate/dicaprate, cocoglyceride, cetearyl isononanoate, isopropyl myristate, isodecyl neopentanoate, tridecyl neopentanoate, C12-15 alkyl benzoate, isopropyl lauroyl sarsosinate, phenethyl benzoate and mixtures thereof.

Paraffins and Hydrocarbon-Based Oils

Suitable paraffins and hydrocarbon-based oils are other than the above-described plant or vegetal oils. They include mineral oil, isoparaffins or C10 to C20 alkanes such as undecane and isododecane.

Polyol(s)

The hair treatment compositions include one or more polyols. The amount of polyol(s) present in the hair treatment composition typically ranges from 0.01 to about 5 wt. %, based on the total weight of the hair treatment composition. For example, the amount of polyol(s) in the hair treatment composition may be about 0.01 to about 5 wt. %, about 0.01 to about 4 wt. %, about 0.01 to about 3 wt. %, about 0.01 to about 2 wt. %, about 0.01 to about 1 wt. %; about 0.05 to about 5 wt. %, about 0.05 to about 4 wt. %, about 0.05 to about 3 wt. %, about 0.05 to about 2 wt. %, about 0.05 to about 1 wt. %; about 0.1 to about 5 wt. %, about 0.1 to about 4 wt. %, about 0.1 to about 3 wt. %, about 0.1 to about 2 wt. %, about 0.1 to about 1 wt. %; about 0.5 to about 5 wt. %, about 0.5 to about 4 wt. %, about 0.5 to about 3 wt. %, about 0.5 to about 2 wt. %, about 0.5 to about 1 wt. %; about 1 to about 5 wt. %, about 1 to about 4 wt. %, about 1 to about 3 wt. %, or about 1 to about 2 wt. %, ranges and subranges therebetween, based on the total weight of the hair treatment composition.

The term "polyol" should be understood as meaning, within the meaning of the present disclosure, an organic molecule comprising at least two free hydroxyl groups. The polyols of the hair treatment composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

The polyols may include, but are not limited to, ethylene glycol, propylene glycol, butylene glycol, hexylene glycol, pentylene glycol, diethylene glycol, dipropylene glycol, 1,3 propanediol, 1,4-butanediol, 1,5-pentanediol, hexane-1,6-diol, glycerin, diglycerin, caprylyl glycol, and a mixture thereof. In some cases, the polyol is chosen from glycerin, diglycerin, glycol, and a mixture thereof. The polyol may be a glycol chosen from ethylene glycol, propylene glycol, butylene glycol, hexylene glycol, pentylene glycol, diethylene glycol, dipropylene glycol, 1,3 propanediol, 1,4-butanediol, 1,5-pentanediol, hexane-1,6-diol, polyethylene glycols, and a mixture thereof.

Polyols that may be included in the hair treatment composition, in certain instances, include ethylene glycol, propylene glycol, butylene glycol, hexylene glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the hair treatment composition comprises at least propylene glycol, and optionally one or more polyols other than propylene glycol.

Non-limiting examples of polyols that may, optionally, be included in the hair treatment include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

Monoalcohol(s)

The hair treatment composition may include or exclude include monoalcohol(s), such as those having 1 to 10 carbons, or from 2 to 6 carbons. In some instances, the amount of monoalcohol present in the hair treatment composition may range from about 1 to about 20 wt. %, based on the total weight of the hair treatment composition. For example, the hair treatment composition may have monoalcohol in an amount of about 0.01 to about 20 wt. %, about 0.01 to about 10 wt. %, about 0.01 to about 5 wt. %, about 0.01 to about 3 wt. %, about 0.01 to about 1 wt. %, including all ranges and sub-ranges therebetween, based on the total weight of the hair treatment composition. The one or more monoalcohols of the hair treatment composition may be chosen from ethanol, propanol, butanol, pentanol, hexanol, isopropyl alcohol, cyclohexanol, isobutyl alcohol, 2-methyl-2-butanol (2-methylbutan-2-ol), and a mixture thereof.

Water

The hair treatment composition typically includes 50 wt. % or more of water. For example, the amount of water present in the hair treatment composition prior to combination with extraneous water may be about 50 wt. % or more, about 55 wt. % or more, about 60 wt. % or more, about 65 wt. % or more, about 70 wt. % or more, about 75 wt. % or more, about 80 wt. % or more, about 85 wt. % or more, about 90 wt. % or more, about 91 wt. % or more, about 92 wt. % or more, about 93 wt. % or more, about 94 wt. % or more, based on the total weight of the hair treatment composition.

PH Adjuster(s)

The hair treatment composition may include one or more pH adjusters to increase or decrease the overall pH of the hair treatment composition. For example, one or more acids may be included to decrease the pH of the hair treatment composition. Examples of suitable acids for decreasing the pH of the hair treatment composition include, but are not limited to, citric acid, acetic acid, and the like. The hair treatment composition may include one or more bases, such as sodium hydroxide, potassium hydroxide and the like, to increase the pH of the hair treatment composition. Additional or alternative acids and bases that are suitable for adjusting the pH of the hair treatment composition are readily known to one of ordinary skill in the art.

As noted above, the pH of the hair treatment composition typically is 2.5 to 5.5. For example, the pH of the hair treatment composition may be from 2.5 to about 5.25, 2.5 to about 5, 2.5 to about 4.75, 2.5 to about 4.5, 2.5 to about 4.25, 2.5 to about 4, 2.5 to about 3.75, 2.5 to about 3.5, 2.5 to about 3.25, 2.5 to about 3; about 2.75 to 5.5, about 2.75 to about 5.25, about 2.75 to about 5, about 2.75 to about 4.75, about 2.75 to about 4.5, about 2.75 to about 4.25, about 2.75 to about 4, about 2.75 to about 3.75, about 2.75 to about 3.5; about 3 to 5.5, about 3 to about 5.25, about 3 to about 5, about 3 to about 4.75, about 3 to about 4.5, about 3 to about 4.25, about 3 to about 4, about 3 to about 3.75; about 3.25 to 5.5, about 3.25 to about 5.25, about 3.25 to about 5, about 3.25 to about 4.75, about 3.25 to about 4.5, about 3.25 to about 4.25, about 3.25 to about 4; about 3.5 to 5.5, about 3.5 to about 5.25, about 3.5 to about 5, about 3.5 to about 4.75, about 3.5 to about 4.5, about 3.5 to about 4.25; about 3.75 to 5.5, about 3.75 to about 5.25, about 3.75 to about 5, about 3.75 to about 4.75, about 3.75 to about 4.5; about 4 to 5.5, about 4 to about 5.25, about 4 to about 5, about 4 to about 4.75; about 4.25 to 5.5, about 4.25 to about 5.25, about 4.25 to about 5; about 4.25 to about 5.25, about 4.25 to about 5, about 4 to about 4.75; about 4.25 to about 5.25, or about 4.25 to about 5, ranges and subranges therebetween.

The amount of the pH adjuster in the hair treatment composition may be based on the desired pH of the final hair treatment composition and/or product. For example, the total amount of the pH adjuster may range from about 0.05 to about 20 wt. %, based on the total weight of the hair treatment composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the hair treatment composition.

The hair treatment compositions of the instant disclosure may be incorporated into a kit. For example, the kits may include at least one hair treatment composition according to the instant disclosure and one or more additional compositions, for example, a shampoo, a conditioner, etc. The various compositions are separately contained in the kits. In some instances, the kits include one or more hair treatment compositions according the instant disclosure, a shampoo, a conditioner a mask, and/or other hair treatment product, all of which are separately contained. Instructions, mixing components, measuring tools, etc., may also optionally be included in the kits.

The compositions may be packaged in a variety of different containers, such as, for example, a ready-to-use container. Non-limiting examples of useful packaging include tubes, jars, caps, unit dose packages, and bottles, including squeezable tubes, bottles, and sprayable containers. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a hair treatment composition according to the instant disclosure, and the other tube may include a composition to be used with the hair treatment composition, for example, a shampoo, a conditioner, an all-in-one shampoo/conditioner (i.e., a conditioning shampoo; also referred to as a "co-wash") mask or other hair treatment products.

Methods of Treating Hair

Aspects of the instant disclosure also relate to methods for making and using such hair treatment compositions. A method for treating and conditioning hair according to aspects of the disclosure typically includes:
(I) applying a hair treatment composition, the hair treatment composition comprising:
(a) about 0.1 to about 10 wt. % of a cationic surfactant;
(b) about 0.1 to about 10 wt. % of a fatty acid having a carbon chain of 12 or more carbons;
    wherein a molar ratio of the total amount of cationic surfactant to the total amount of fatty acid is 1:1.05 to 1:3,
(c) about 0.1 to about 20 wt. % of a fatty alcohol; and
(d) about 50 wt. % or more of water,
    wherein the hair treatment composition has a pH of about 2.5 to about 5.5, and all weight percentages are based on the total weight of the hair treatment composition, and
(II) rinsing the hair treatment composition from the hair.

The methods for treating and/or conditioning hair according to the disclosure may vary, but typically include applying a hair treatment composition as disclosed herein, allowing the hair treatment composition to remain on the hair for a sufficient amount of time, and rinsing the hair treatment compositions from the hair. The hair treatment composition may be applied to the hair in a sequence with other compositions. For example, the hair treatment composition may be applied to the hair (wet or dry) before shampooing the hair, after shampooing the hair, before applying a conditioner to the hair, and/or after applying a conditioning to the hair, etc. The hair treatment compositions, however, are not required to be used in a sequence.

In some cases, the hair treatment compositions are used in conjunction with additional hair treatment compositions in a routine, for example, during an individual's normal showering/bathing routine. The hair treatment composition may be applied to the hair individually or may be combined with one or more additional compositions. For instance, the hair treatment composition may be mixed with a shampoo (or conditioner) prior to application to the hair. In this case, the mixture of the shampoo (or conditioner) and the hair treatment composition are simultaneously applied to the hair during the cleansing or conditioning process and simultaneously rinsed from the hair. Alternatively, the hair treatment composition may be layered on top of (or lathered into) hair to which a shampoo (or conditioner) has already been applied or vice versa. In this case, the shampoo (or conditioner) may be first applied to the hair and without rinsing the shampoo (or conditioner) from the hair, the hair treatment composition is also applied to the hair. Alternatively, the hair treatment composition may be applied to the hair and without rinsing it from the hair, a shampoo (or conditioner) is then subsequently applied to the hair.

When used in conjunction with a shampoo and/or a conditioner, the hair treatment composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair treatment composition of the instant disclosure:shampoo/conditioner, etc.).

The hair treatment compositions of the instant disclosure may be allowed to remain on the hair for a minimum amount of time before being rinsed from the hair, but it is not necessary to allow the hair treatment composition to remain on the hair for an extended period of time. Conveniently, the hair treatment compositions can be applied and allowed to remain on the hair for a period of time that is typical for regular shampooing and/or conditioning. For example, the hair treatment composition (whether combined with another hair-treatment composition such as a shampoo or conditioner) may be applied to the hair and allowed to remain on the hair for a few seconds (1, 2, 3, or 5 seconds) up to about 1 minute, about 2 minutes, about 5 minutes, about 10 minutes, about 15 minutes, about 20 minutes, about 25 minutes, or about 30 minutes.

When the hair treatment composition is not being mixed with another composition prior to application to the hair, the hair treatment composition may be applied to the hair immediately after or before the hair is treated with another composition (e.g., a shampoo and/or a conditioner). For example, the hair treatment compositions may be applied to the hair within about a few seconds or 1, 2, 5, 10, or 20 minutes before or after a shampoo and/or a conditioner is applied to the hair.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair treatment compositions of the instant disclosure can be free or essentially free of all components and elements positively recited throughout the instant disclosure. In some instances, the hair treatment compositions of the present disclosure may be substantially free of non-incidental amounts of the ingredient(s) or compound(s) described herein. A non-incidental amount of an ingredient or compound is the amount of that ingredient or compound that is added into the hair treatment composition by itself. For example, a hair treatment composition may be substantially free of a non-incidental amount of an ingredient or compound, although such ingredient(s) or compound(s) may be present as part of a raw material that is included as a blend of two or more compounds.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

Some of the various categories of components identified may overlap. In such cases where overlap may exist and the hair treatment composition includes both components (or the composition includes more than two components that overlap), an overlapping compound does not represent more than one component. For example, certain compounds may be characterized as both an emollient and a fatty compound. If a particular hair composition includes both an emollient and a fatty compound, the compounds that may be characterized as both an emollient and a fatty compound will serve only as either the emollient or the fatty compound—not both.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations. Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

EMBODIMENTS OF THE DISCLOSURE

In certain embodiments, the hair treatment compositions of the instant disclosure include:
  about 0.1 to about 10 wt. %, preferably about 0.1 to about 4 wt. %, more preferably about 0.5 to about 3 wt. %, of a cationic surfactant, such as those chosen from chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof;
  about 0.1 to about 10 wt. %, preferably about 0.1 to about 5 wt. %, more preferably about 0.5 to about 4 wt. %, of a fatty acid having a carbon chain of 12 or more carbons including, e.g., lauric acid, myristic acid, palmitic acid, stearic acid, oleic acid, linoleic acid, ricinoleic acid, arachidic acid, and behenic acid;
  wherein a molar ratio of the total amount of cationic surfactant to the total amount of fatty acid is about 1:0.5 to about 1:3, preferably about 1:0.9 to about 1:1.5, or more preferably about 1:1 to about 1:1.5,
  about 0.1 to about 20 wt. %, preferably about 1 to about 15 wt. %, more preferably about 1.5 to about 10 wt. %, of a fatty alcohol, such as those chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, or myricyl alcohol, and a mixture thereof; and
  about 50 wt. % or more, preferably about 60 wt. % or more, more preferably about 75 wt. % or more, of water, wherein the hair treatment composition has a pH of about 2.5 to about 5.5, and all weight percentages are based on the total weight of the hair treatment composition.

In further embodiments, the hair treatment compositions of the instant disclosure consist of:

about 0.1 to about 10 wt. %, preferably about 0.1 to about 4 wt. %, more preferably about 0.5 to about 3 wt. %, of a cationic surfactant, such as those chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof;

about 0.1 to about 10 wt. %, preferably about 0.1 to about 5 wt. %, more preferably about 0.5 to about 4 wt. %, of a fatty acid having a carbon chain of 12 or more carbons including, e.g., lauric acid, myristic acid, palmitic acid, stearic acid, oleic acid, linoleic acid, ricinoleic acid, arachidic acid, and behenic acid;

wherein a molar ratio of the total amount of cationic surfactant to the total amount of fatty acid is about 1:0.5 to about 1:3, preferably about 1:0.9 to about 1:1.5, or more preferably about 1:1 to about 1:1.5, about 0.1 to about 20 wt. %, preferably about 1 to about 15 wt. %, more preferably about 1.5 to about 10 wt. %, of a fatty alcohol, such as those chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, or myricyl alcohol, and a mixture thereof;

about 50 wt. % or more, preferably about 60 wt. % or more, more preferably about 75 wt. % or more, of water;

optionally, about 0.1 to about 10 wt. %, preferably about 0.5 to about 8 wt. %, more preferably about 1 to about 6 wt. %, of a silicone, such as those chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), dimethicone copolyols, dimethicone copolyol esters, dimethicone copolyol quaternium nitrogen containing compounds, dimethicone copolyol phosphate esters, silicone quaternium-18, and a mixture thereof;

optionally, about 0.01 to about 5 wt. %, preferably about 0.01 to about 4 wt. %, more preferably about 0.05 to about 4 wt. %, of a polymer, such as those chosen from polysaccharides, polyamines, acrylate polymers, polyurethanes, or a combination thereof;

optionally, about 0.01 to about 10 wt. %, preferably about 0.01 to about 4 wt. %, more preferably about 0.05 to about 4 wt. %, of a fatty compound other than fatty alcohols and fatty acids having a carbon chain of 12 or more carbons, such as those chosen from coconut oil, soybean oil, rapeseed oil, cottonseed oil, olive oil, palm oil, peanut oil, avocado oil, hazel nut oil, grapeseed oil, colza oil, cade oil, peach kernel oil, coffee bean oil, jojoba oil, caprylic/capric triglyceride, isopropyl myristate, PPG-3 myristyl ether, isopropyl palmitate, dibutyl adipate, propyleneglycol dicaprylate/dicaprate, cocoglyceride, cetearyl isononanoate, isopropyl myristate, isodecyl neopentanoate, tridecyl neopentanoate, $C_{12-15}$ alkyl benzoate, isopropyl lauroyl sarsosinate, phenethyl benzoate, $C_{15}$-$C_{19}$ alkanes, squalane, and a mixture thereof; and optionally, about 0.01 to about 5 wt. %, preferably about 0.01 to about 4 wt. %, more preferably about 0.05 to about 4 wt. %, of a polyol, including, e.g., glycerin, diglycerin, ethylene glycol, propylene glycol, butylene glycol, hexylene glycol, pentylene glycol, diethylene glycol, dipropylene glycol, 1,3 propanediol, 1,4-butanediol, 1,5-pentanediol, hexane-1,6-diol, polyethylene glycols, and a mixture thereof, wherein the hair treatment composition has a pH of about 2.5 to about 5.5, and all weight percentages are based on the total weight of the hair treatment composition.

In additional embodiments, a method is provided for treating hair including:

(I) applying a hair treatment composition, the hair treatment composition comprising:

about 0.1 to about 10 wt. %, preferably about 0.1 to about 4 wt. %, more preferably about 0.5 to about 3 wt. %, of a cationic surfactant, such as those chosen from chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof;

about 0.1 to about 10 wt. %, preferably about 0.1 to about 5 wt. %, more preferably about 0.5 to about 4 wt. %, of a fatty acid having a carbon chain of 12 or more carbons including, e.g., lauric acid, myristic acid, palmitic acid, stearic acid, oleic acid, linoleic acid, ricinoleic acid, arachidic acid, and behenic acid;

wherein a molar ratio of the total amount of cationic surfactant to the total amount of fatty acid is about 1:0.5 to about 1:3, preferably about 1:0.9 to about 1:1.5, or more preferably about 1:1 to about 1:1.5, about 0.1 to about 20 wt. %, preferably about 1 to about 15 wt. %, more preferably about 1.5 to about 10 wt. %, of a fatty alcohol, such as those chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, or myricyl alcohol, and a mixture thereof; and about 50 wt. % or more, preferably about 60 wt. % or more, more preferably about 75 wt. % or more, of water, wherein the hair treatment composition has a pH of about 2.5 to about 5.5, and all weight percentages are based on the total weight of the hair treatment composition.

(II) rinsing the hair treatment composition from the hair.

EXAMPLES

Implementation of the present disclosure is provided by way of the following examples. The following examples serve to elucidate aspects of the technology without being limiting in nature.

Example 1

TABLE 1

| | | US INCI Name | Ex. A | Ex. B | Ex. C | Ex. D | Ex. E | Ex. F | Ex. G |
|---|---|---|---|---|---|---|---|---|---|
| (a) | Cationic Surfactant | BEHENTRIMONIUM CHLORIDE | | 1.23 | 1.05 | 1.05 | 1.23 | 1.23 | 1.23 |
| | | STEARAMIDOPROPYL DIMETHYLAMINE | 1 | | | | | | |
| | | CETRIMONIUM CHLORIDE | | | | | | | 0.02 |
| (b) | Fatty Acid | MYRISTIC ACID | 0.02 | 0.03 | 0.02 | 0.02 | 0.03 | 0.03 | 0.03 |
| | | PALMITIC ACID | 0.26 | 0.37 | 0.31 | 0.25 | 0.46 | 0.46 | 0.46 |
| | | STEARIC ACID | 0.31 | 0.45 | 0.37 | 0.30 | 0.56 | 0.56 | 0.56 |
| | Molar ratio of cationic surfactant(s) to fatty acid(s) | | 1:0.81 | 1:1.04 | 1:1 | 1:0.81 | 1:1.28 | 1:1.28 | 1:1.25 |
| (c) | Fatty Alcohol | CETEARYL ALCOHOL | 3.41 | 4.16 | 3.54 | 3.68 | 3.95 | 3.95 | 3.95 |
| (e) | Silicone | AMODIMETHICONE | | | 1 | 1 | 1 | 1 | 1 |
| (f) | Polymer | CETYL HYDROXYETHYL-CELLULOSE | | | | | | | |
| (g) | emollient | COCOS NUCIFERA OIL | | | | | | 0.7 | 0.7 |
| | | HYDROGENATED VEGETABLE OIL | | | | | | | |
| (h) | Polyol Monoalcohol | CAPRYLYL GLYCOL | 0.3 | 0.3 | 0.3 | 0.3 | 0.3 | 0.3 | 0.3 |
| | | ISOPROPYL ALCOHOL | | 0.28 | 0.24 | 0.24 | 0.28 | 0.28 | 0.28 |
| | Amino acid | ARGININE | | 0.2 | 0.2 | 0.2 | 0.21 | 0.21 | 0.21 |
| | pH Adjuster | TARTARIC ACID | 0.13 | | | | | | |
| | Misc. | FRAGRANCE, BENZOIC ACID, SODIUM BENZOATE, HYDRATED SILICA, SILICA DIMETHYL SILYLATE, POLYSORBATE 60, and/or TRIDECETH-6 | 1 | 1 | 0.2 | 0.2 | 1 | 1 | 1.09 |
| (d) | Water | Water | 93.57 | 91.99 | 92.77 | 92.76 | 90.98 | 90.28 | 90.17 |

| | | US INCI Name | Ex. H | Ex. I | Ex. J | Ex. K | Ex. L | Ex. M | Ex. N |
|---|---|---|---|---|---|---|---|---|---|
| (a) | Cationic Surfactant | BEHENTRIMONIUM CHLORIDE | | 1.23 | 1.23 | 1.23 | 0.99 | 1.23 | 1.23 |
| | | STEARAMIDOPROPYL DIMETHYLAMINE | 1 | | | | | | |
| | | CETRIMONIUM CHLORIDE | | | 0.02 | 0.2 | | | |
| (b) | Fatty Acid | MYRISTIC ACID | 0.02 | 0.03 | 0.04 | 0.05 | 0.02 | 0.02 | 0.02 |
| | | PALMITIC ACID | 0.32 | 0.46 | 0.55 | 0.74 | 0.24 | 0.3 | 0.3 |
| | | STEARIC ACID | 0.39 | 0.56 | 0.67 | 0.89 | 0.29 | 0.36 | 0.36 |
| | Molar ratio of cationic surfactant(s) to fatty acid(s) | | 1:1 | 1:1.28 | 1:154 | 1:2.05 | 1:0.83 | 1:0.82 | 1:0.82 |
| (c) | Fatty Alcohol | CETEARYL ALCOHOL | 3.27 | 3.95 | 3.74 | 3.95 | 3.46 | 4.33 | 4.33 |
| (e) | Silicone | AMODIMETHICONE | | 1 | 1 | | | | |
| (f) | Polymer | CETYL HYDROXYETHYL-CELLULOSE | | | | | | | 0.1 |
| (g) | emollient | COCOS NUCIFERA OIL | | 1.5 | 0.7 | | | | |
| | | HYDROGENATED VEGETABLE OIL | 0.5 | | | | | | |
| (h) | Polyol Monoalcohol | CAPRYLYL GLYCOL | 0.3 | 0.3 | 0.3 | 0.3 | 0.3 | 0.3 | 0.3 |
| | | ISOPROPYL ALCOHOL | | 0.28 | 0.28 | 0.28 | 0.23 | 0.28 | 0.28 |

TABLE 1-continued

| | | | | | | | | |
|---|---|---|---|---|---|---|---|---|
| Amino acid | ARGININE | | 0.21 | 0.25 | | 0.19 | 0.19 | 0.19 |
| pH Adjuster | TARTARIC ACID | 0.16 | | | | | | |
| Misc. | FRAGRANCE, BENZOIC ACID, SODIUM BENZOATE, HYDRATED SILICA, SILICA DIMETHYL SILYLATE, POLYSORBATE 60, and/or TRIDECETH-6 | 1 | 1.09 | 1.09 | 1 | 1 | 1 | 1 |
| (d) Water | Water | 93.04 | 89.37 | 90.13 | 91.56 | 93.30 | 91.99 | 91.89 |

Example 2

Example Composition E was evaluated in comparison to Comparative Composition 1. The formulation for Comparative Composition 1 is provided below in the table below.

TABLE 2

| | US INCI Name | Comp. 1 |
|---|---|---|
| (a) Cationic Surfactant(s) | BEHENTRIMONIUM CHLORIDE and/or CETRIMONIUM CHLORIDE | 2.4 |
| (c) Fatty Alcohol | CETEARYL ALCOHOL | 6 |
| (e) Silicone | AMODIMETHICONE | 0.5 TO 1 |
| (h) Polyol | CAPRYLYL GLYCOL | <0.01 |
| Monoalcohol | ISOPROPYL ALCOHOL | <1 |
| Fatty esters | CETYL ESTERS | 0.5 TO 1 |
| Active Agents | NIACINAMIDE, PYRIDOXINE HCl, CAMELLIA SINENSIS LEAF EXTRACT, PYRUS MALUS (APPLE) FRUIT EXTRACT, CITRUS LIMON (LEMON) FRUIT EXTRACT, SACCHARUM OFFICINARUM (SUGARCANE) EXTRACT, LEUCONOSTOC/RADISH ROOT FERMENT FILTRATE, and HYDROXYPROPYLTRIMONIUM LEMON PROTEIN, 2-OLEAMIDO-1,3-OCTADECANEDIOL | <0.5 |
| Misc. | FRAGRANCE, SODIUM BENZOATE, PHENOXYETHANOL, TRIDECETH-6, and CHLORHEXIDINE DIGLUCONATE, pH ADJUSTER | <2 |
| (d) | WATER | QS 100 |

Example Composition E and Comparative Composition 1 were applied to 10 volunteers having hair type 3-5 sensitivity (medium to high damage hair). Each of the volunteers had their hair washed with a shampoo, rinsed, and wringed to remove any excess water before the application of Example Composition E and Comparative Composition 1. Example Composition E was applied to a first half of each volunteer's head of hair while Comparative Composition 1 was applied to the other half of each volunteer's head of hair.

During the application of the hair treatment compositions, Example Composition E exhibited noticeably higher in melting sensation, slightly higher absorption, detangling, and suppleness in comparison to Comparative Composition 1. However, Example Composition E was slightly less sticky than Comparative Composition 1.

After rinsing each of the volunteer's hair, Example Composition E exhibited slightly better detangling, combing, suppleness, and smoothness as compared to Comparative Composition 1 for the evaluation of the wet hair results. Comparative Composition 1, however, exhibited slightly better wet root lift and individualized and mass effect than Example Composition E for the wet hair results.

The hair of each volunteer was subsequently dried using a blow dryer and evaluated. Example Composition E exhibited slightly better smooth hair (visual and tactile) and slightly improved dryness and dry ends than Comparative Composition 1. Example Composition E exhibits slightly higher weight of the hair and coating amount, but slightly less mass effect and clean hair feel than Comparative Composition 1 for the dry hair results.

Example 3

The viscosity as a function of shear rate of Example Compositions E and F and Comparative Compositions 1 and 2 were evaluated under non-diluted and diluted conditions. The formulation for Comparative Composition 2 is provided below in Table 3.

TABLE 3

| | INCI US Name | Comp. 2 |
|---|---|---|
| Cationic Surfactant | CETRIMONIUM CHLORIDE/ DICETYLDIMONIUM CHLORIDE | 2 |
| Fatty Alcohol | CETEARYL ALCOHOL | 6 |
| Fatty Esters | CETYL ESTERS | 0.5 TO 1 |
| Monoalcohol | ISOPROPYL ALCOHOL | <1 |
| Active Agents | PANTHENOL, NIACINAMIDE, HYDROLYZED WHEAT PROTEIN, HYDROLYZED SOY PROTEIN, HYDROLYZED CORN PROTEIN, HYDROXYPROPYLTRIMONIUM HYDROLYZED WHEAT PROTEIN, and RICINUS COMMUNIS (CASTOR) SEED OIL | <0.5 |
| Silicone | AMODIMETHICONE/DIMETHICONE | 1 |
| Misc. | PEG-100 STEARATE, TRIDECETH-3, TRIDECETH-10, STEARETH-6, PHENOXYETHANOL, TRISODIUM HEDTA, SODIUM BENZOATE, CHLORHEXIDINE DIGLUCONATE, TARTARIC ACID, ACETIC ACID | 0.5 TO 1 |
| Fragrance | FRAGRANCE | <1 |
| Water | WATER | QS 100 |

Under non-diluted conditions, samples of Example Compositions E and F and Comparative Compositions 1 and 2 were tested using a TA instrument Discovery HR-2 rheometer. For diluted conditions, diluted samples were prepared by combining each of Example Compositions E and F and Comparative Compositions 1 and 2 with water in a weight ratio of (1:1.5) and were tested using a TA instrument Discovery HR-2. FIGS. 1A-1D provide graphs of the viscosity of the non-diluted and diluted samples of Example Compositions E and F and Comparative Compositions 1 and 2 as a function shear rate.

Figure 1B:
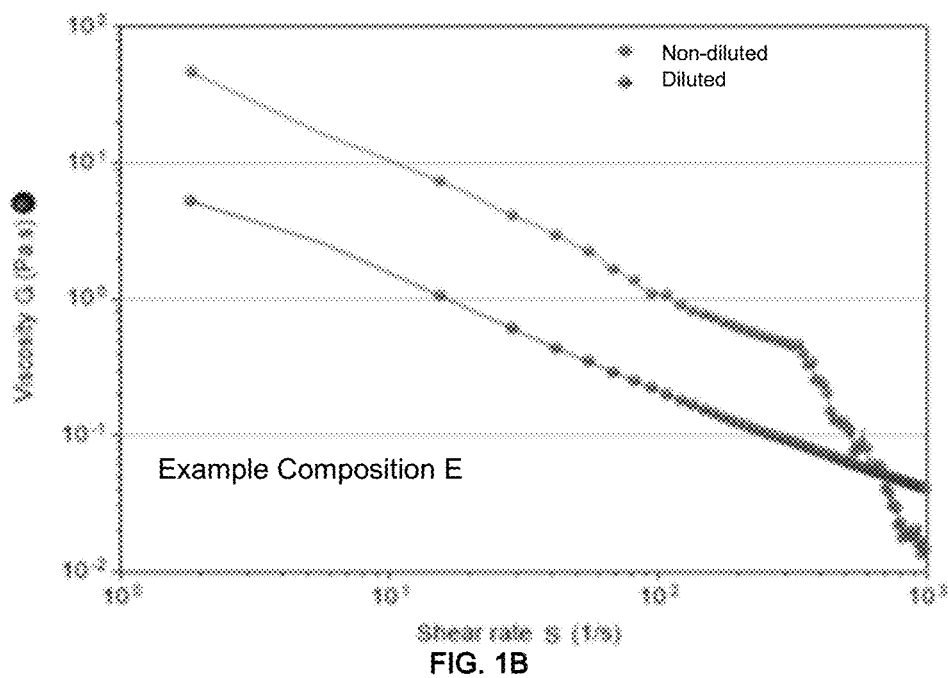

As seen in FIGS. 1A and 1B, the viscosity as a function of shear rate of the diluted samples of Example Compositions E and F were significantly less than the viscosity as a function of shear rate of the non-diluted samples of Example Compositions E and F. The decrease in viscosity due to dilution, which mimics the application onto wet hair and/or the addition of extraneous water, is associated with the unique melting sensory provided by exemplary hair treatment compositions of the instant disclosure. As noted in Example 2, above, Example Composition E exhibited noticeably higher melting sensation.

Figure 1C:
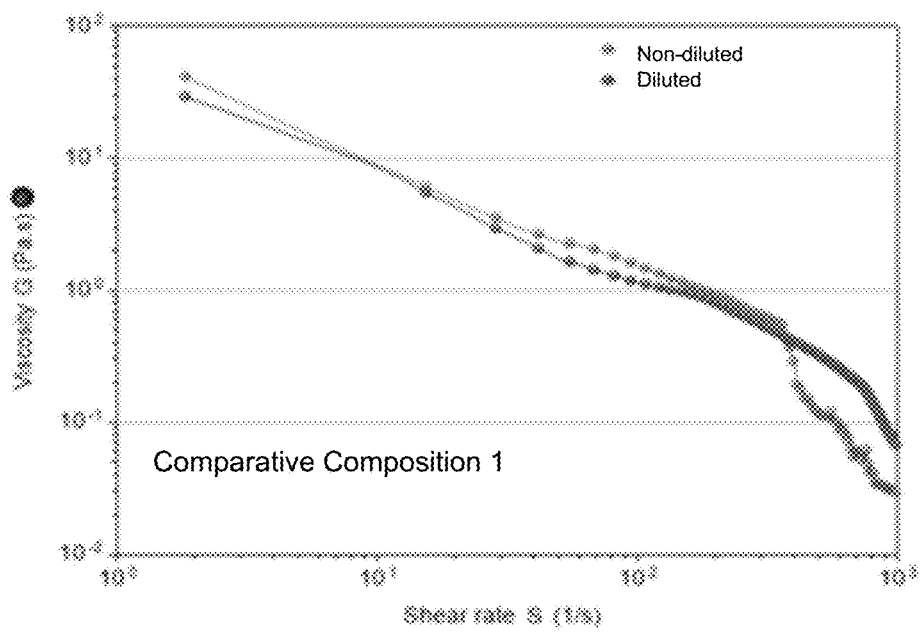
Figure 1D:
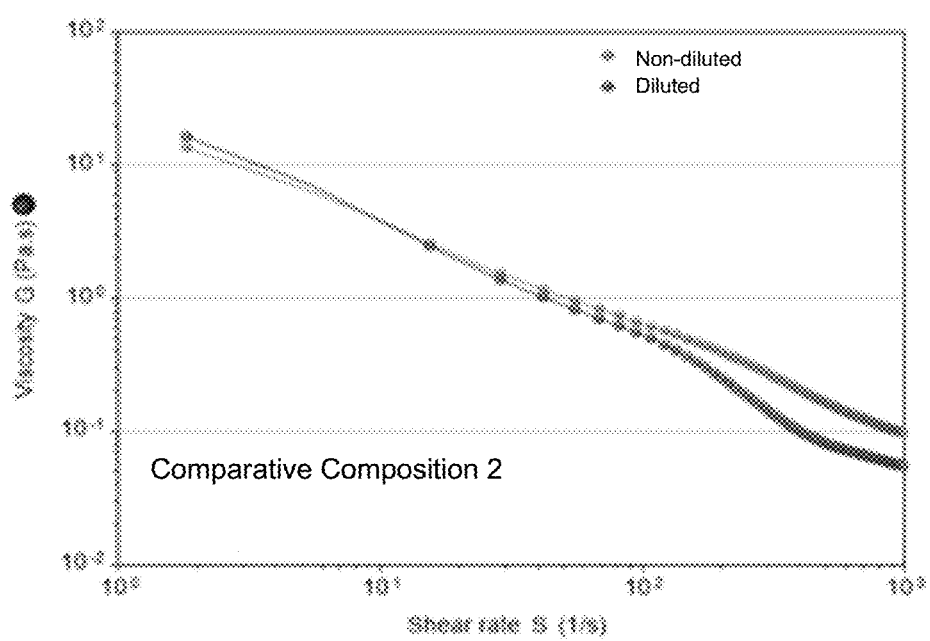

Comparative Compositions 1 and 2, however, exhibited a similar viscosity as a function of shear rate for the non-diluted samples and the diluted samples (see FIGS. 1C and 1D). Thus, Example Compositions E and F exhibited a surprising change in viscosity behavior after dilution.

Example 4

Figure 2A:
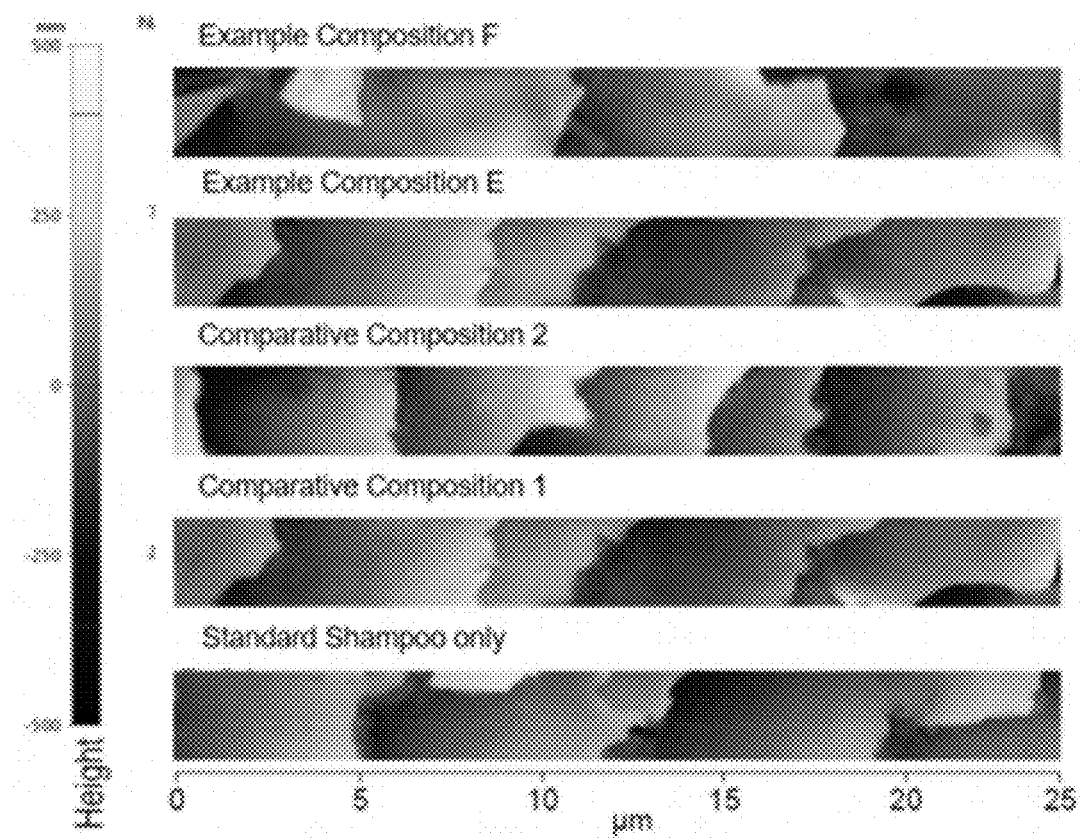
FIGS. 2A and 2B show images of the hair surface topography and stiffness after application of comparative compositions and example compositions to hair according to aspects of the disclosure.
Figure 2B:
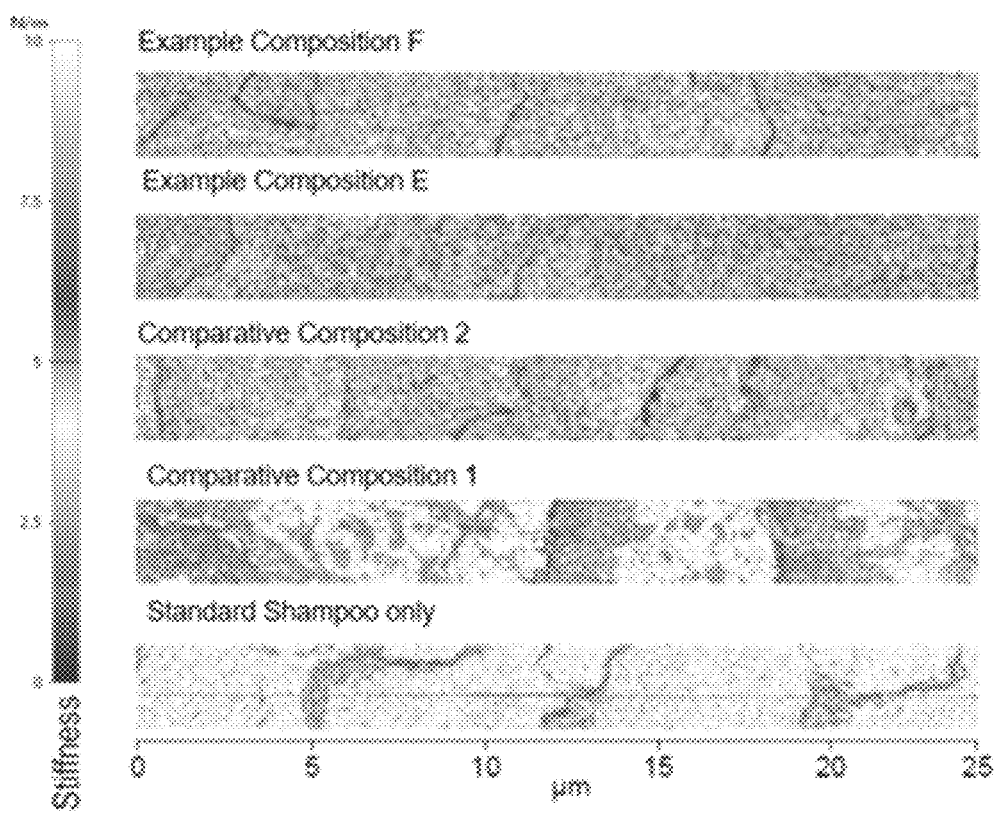

Example Compositions E and F and Comparative Compositions 1 and 2 were assessed to determine the uniformity of deposition coverage on medium bleached hair swatches using PARK SYSTEMS NX10 Atomic Force Microscopy. The medium bleached hair swatches were washed with a standard shampoo before the application of Example Compositions E and F and Comparative Compositions 1 and 2. The swatches were then rinsed and dried. FIGS. 2A and 2B show images of the hair surface topography and stiffness after application of Example Compositions E and F and Comparative Compositions 1 and 2. The uniformity of coverage for Example Compositions E and F were better than both Comparative Compositions 1 and 2.

What is claimed is:

1. A hair treatment composition comprising:
   (a) about 0.5 to about 8 wt. % of one or more cationic surfactants;
   (b) about 0.5 to about 5 wt. % of one or more fatty acids having a carbon chain length of 12 or more carbon atoms;
      wherein molar amounts of (a) and (b) are in a ratio of about 1:0.8 to about 1:2.1 ((a):(b)); and
      the one or more cationic surfactants of (a) have a carbon chain length within 10 carbon atoms of the carbon chain length of the one or more fatty acids of (b);
   (c) about 1 to about 10 wt. % of one or more fatty alcohols having a carbon chain length of 12 or more carbon atoms;
   (d) about 50 wt. % or more of water;
   (e) optionally, about 0.1 to about 10 wt. % of one or more silicones;
   (f) optionally, about 0.01 to about 5 wt. % of one or more polymers;
   (g) optionally, about 0.01 to about 10 wt. % of one or more fatty compounds other than the one or more fatty alcohols of (c) and the one or more fatty acids of (b); and
   (h) about 0.01 to about 5 wt. % of one or more polyols;
      wherein the hair treatment composition comprises a lamellar gel network,
      the hair treatment composition has a pH lower than the pKa of the one or more fatty acids of (b) and is in a range of about 2.5 to about 5.5,
      increasing the pH of the hair treatment composition above the pKa of the one or more fatty acids of (b) destabilizes the lamellar gel network, and
      all weight percentages are based on a total weight of the hair treatment composition.

2. A method for treating hair comprising:
   (I) applying a hair treatment composition of claim 1 to the hair, and
   (II) rinsing the hair treatment composition from the hair.

3. A hair treatment composition comprising:
   (a) about 0.5 to about 8 wt. % of one or more cationic surfactants;
   (b) about 0.5 to about 5 wt. % of one or more fatty acids having a carbon chain length of 12 to 22 carbon atoms;
      wherein molar amounts of (a) and (b) are in a ratio of about 1:0.5 to about 1:3 ((a):(b)), and
      the one or more cationic surfactants of (a) have a carbon chain length within 10 carbon atoms of the carbon chain length of the one or more fatty acids of (b);
   (c) about 1 to about 10 wt. % of one or more fatty alcohols having a carbon chain length of 12 or more carbon atoms; and
   (d) about 50 wt. % or more of water,
      wherein the hair treatment composition has a pH lower than the pKa of the one or more fatty acids of (b) and is in a range of about 2.5 to about 5.5,
      the hair treatment composition comprises a lamellar gel network,
      increasing the pH of the hair treatment composition above the pKa of the one or more fatty acids destabilizes the lamellar gel network, and
      all weight percentages are based on a total weight of the hair treatment composition.

4. A hair treatment composition comprising:
   (a) about 0.5 to about 8 wt. % of one or more cationic surfactants;
   (b) about 0.5 to about 5 wt. % of one or more fatty acids having a carbon chain length of 12 to 22 carbon atoms;
      wherein molar amounts of (a) and (b) are in a ratio of about 1:0.5 to about 1:3 ((a):(b)), and
      the one or more cationic surfactants of (a) have a carbon chain length within 10 carbon atoms of the carbon chain length of the one or more fatty acids of (b);
   (c) about 1 to about 10 wt. % of one or more fatty alcohols having a carbon chain length of 12 or more carbon atoms; and
   (d) about 50 wt. % or more of water;
   (e) less than 0.1 wt. % of a fatty amidoamine compound; and
   (f) less than 0.1 wt. % of a PEGylated compound,
      wherein the hair treatment composition has a pH lower than the pKa of the one or more fatty acids of (b) and is in a range of about 2.5 to about 5.5,
      the hair treatment composition comprises a lamellar gel network,
      increasing the pH of the hair treatment composition above the pKa of the one or more fatty acids destabilizes the lamellar gel network, and
      all weight percentages are based on a total weight of the hair treatment composition.

* * * * *